(12) United States Patent
Zander et al.

(10) Patent No.: US 7,591,819 B2
(45) Date of Patent: Sep. 22, 2009

(54) BONE NAIL

(75) Inventors: Nils Zander, Eckernförde (DE); Axel Cremer, Fahrenkrog (DE)

(73) Assignee: Stryker Trauma GmbH (DE)

( * ) Notice: Subject to any disclaimer, the term of this patent is extended or adjusted under 35 U.S.C. 154(b) by 787 days.

(21) Appl. No.: 10/869,190

(22) Filed: Jun. 16, 2004

(65) Prior Publication Data

US 2004/0260290 A1 Dec. 23, 2004

(30) Foreign Application Priority Data

Jun. 18, 2003 (DE) .......................... 203 09 399 U

(51) Int. Cl.
*A61B 17/58* (2006.01)

(52) U.S. Cl. .................... 606/64; 606/62; 411/508; 411/509; 411/510

(58) Field of Classification Search ........... 606/62–64, 606/68, 304, 310, 314, 323; 249/80; 411/506, 411/508–510, 393, 95; 403/276, 282
See application file for complete search history.

(56) References Cited

U.S. PATENT DOCUMENTS

| 4,402,641 | A | * | 9/1983 | Arff ........................... 411/510 |
| 5,176,681 | A |   | 1/1993 | Lawes et al. |
| 5,308,205 | A | * | 5/1994 | Lautenschlager ........... 411/182 |
| 5,319,839 | A | * | 6/1994 | Shimajiri ..................... 24/453 |
| 5,713,901 | A | * | 2/1998 | Tock ............................ 606/62 |
| 5,800,109 | A | * | 9/1998 | Carruthers ................... 411/510 |
| 6,039,523 | A | * | 3/2000 | Kraus .......................... 411/48 |
| 6,126,661 | A |   | 10/2000 | Faccioli et al. |
| 6,235,031 | B1 | * | 5/2001 | Hodgeman et al. ............. 606/64 |
| 6,402,753 | B1 | * | 6/2002 | Cole et al. ..................... 606/62 |
| 2006/0084999 | A1 | * | 4/2006 | Aschmann .................... 606/64 |
| 2006/0111717 | A1 | * | 5/2006 | Saueressig et al. ............ 606/64 |
| 2007/0134073 | A1 | * | 6/2007 | Shereyk et al. .............. 411/510 |

FOREIGN PATENT DOCUMENTS

| DE | 195 05 609 | A1 |   | 8/1996 |
| EP | 0 257 118 | A1 |   | 8/1986 |
| EP | 0 321 170 | A1 |   | 12/1988 |
| EP | 1175872 |   |   | 1/2002 |
| GB | 2209947 |   |   | 6/1989 |
| JP | 2005007170 | A | * | 1/2005 |
| RU | 2172621 | C2 | * | 8/2005 |
| WO | 03/094763 |   |   | 11/2003 |

* cited by examiner

*Primary Examiner*—Eduardo C Robert
*Assistant Examiner*—Julianna N Harvey
(74) *Attorney, Agent, or Firm*—Lerner, David, Littenberg, Krumholz & Mentlik, LLP

(57) ABSTRACT

A bone nail, particularly a proximal femoral nail, has a nail shank having at least one cross-bore near one end and an axial bore having a threaded portion. A screw, for example, a femoral neck screw is provided having a threaded portion and a smooth shank portion between the threaded portion and a screw head, which can be introduced into the cross-bore. An interlocking pin or screw is placed in the axial bore. The locking pin has a male threaded portion interacting with the female threaded portion of the bore. The locking pin or screw has an end portion which engages the smooth shank of the screw to locate it axially and wherein at least the end portion of the locking pin is made of an elastically and/or plastically deformable material.

17 Claims, 2 Drawing Sheets

BONE NAIL

BACKGROUND OF THE INVENTION

The invention relates to a bone nail, particularly a proximal femoral nail. In particular, the invention relates to an axially moveable locking screw for fixing a femoral neck screw in a desired location.

To take care of trochanteric fractures of the femur, it is known to drive an interlocking nail into the femur from the proximal end and to provide the nail shank with a slanting cross-bore through which a femoral neck screw is passed. It is also known to screw an interlocking pin into the interlocking nail that interacts with the femoral neck screw to selectively fix the screw in place axially and/or rotationally.

In conjunction with an implant of this type, it has also become known to provide two parallel neck screws penetrating the nail at an angle. The uppermost one of the two screws is prevented from axially slipping away by means of an interlocking pin or screw mounted in the axis of the nail for axial movement therealong.

SUMMARY OF THE INVENTION

It is the object of the intention to improve a bone nail, particularly of the type described above to the effect that an efficient axial location of a screw traversing the bone nail crosswise be obtained without causing damage to the screw.

In the inventive bone nail, at least the free end portion of the interlocking pin is formed from an elastically and/or plastically deformable material.

According to a preferred aspect of the invention, the interlocking pin or screw, or at least its end portion, is made of a plastic material. Alternatively, an aspect of the invention provides that the end portion be made of an elastically deformable material, e.g. a suitable metal, the end portion being formed in such a way that the region coming into engagement with the femoral neck screw is deformed in an elastically compliant fashion in each rotational position of the interlocking screw or pin.

The formation of the elastically deformable engagement region can be effected in various ways. To this end, an aspect of the invention provides that the interlocking portion of the screw or pin has a disc-shaped portion which is axially spaced from the adjacent part of the end portion and is joined to a central core portion of the interlocking pin. The disc edge which comes into engagement with the shank of the femoral neck screw or another interlocking screw is preferably rounded to prevent it from digging into the material of the femoral neck screw.

Preferably, a plurality of parallel axial disc-shaped portions are provided which are joined to the core portion. The core portion can preferably increase in its diameter gradually from the free end of the interlocking pin towards the driven end.

According to another aspect of the invention, it is provided that the interlocking pin has a stop face at the circumference which interacts with an abutment in the axial bore of the nail. This creates a limiting abutment where the femoral neck screw can always be safely interlocked although there is a fixed abutment and there are tolerances.

According to a further aspect of the invention, the interlocking pin has a smooth portion at the end opposed to the free end portion that is approximately fittingly seated in the bore of the nail shank and has an end surface approximately flush with the end of the bone nail shaft when the interlocking pin is in engagement or bears on the abutment in the bore. The end of the bone nail bore preferably has a female threaded portion and the pin has a male threaded portion. The male threaded portion of the interlocking pin is between the smooth portion and the end portion.

These and other objects of the invention are achieved by a bone nail having a nail shank with at least one cross-bore adjacent a first end and an axial bore therein having a threaded portion. At least one femoral neck screw is provided for insertion into the at least one bore which screw has a threaded portion and a smooth shank portion between the threaded portion and a screw head. It is possible to utilize two femoral neck screws and two cross-bores in the nail shank. A locking pin or screw having a male threaded portion interacts with the female threaded portion of the nail bore and has an end portion which engages the smooth shank of the femoral neck screw to locate it axially within the bore. At least that end portion of the locking pin or screw is made of an elastically and/or plastically deformable material.

The end portion of the locking pin is preferably formed from the elastic material and has a compliant locking portion for engaging the screw in every rotational position of the locking pin. The interlocking portion of the pin preferably has a disc-shaped portion which is axially spaced from the adjacent part of the end portion and is joined to a central core portion of the locking screw or pin. Preferably, the pin end portion includes a plurality of parallel axially spaced disc-shaped portions which are joined to the core portion. If the core portion is made of metal, the plastic disc portion can be molded with a central receptacle or cup and placed on the metal core portion. Alternately, the entire pin may be molded from a polymeric material. The locking pin or screw has a first driven end and a second free end which contacts the femoral neck screw smooth shaft portion. Preferably, the outer diameter of a second pin end remains constant while a tapering core causes the radial extent of each disc from the core to increase on moving from the first to the second pin end, i.e. the core widens on moving from the second end towards the first end.

BRIEF DESCRIPTION OF THE DRAWINGS

The invention will be described in more detail below with reference to an embodiment illustrated in the drawings.

DETAILED DESCRIPTION

Figure 1:
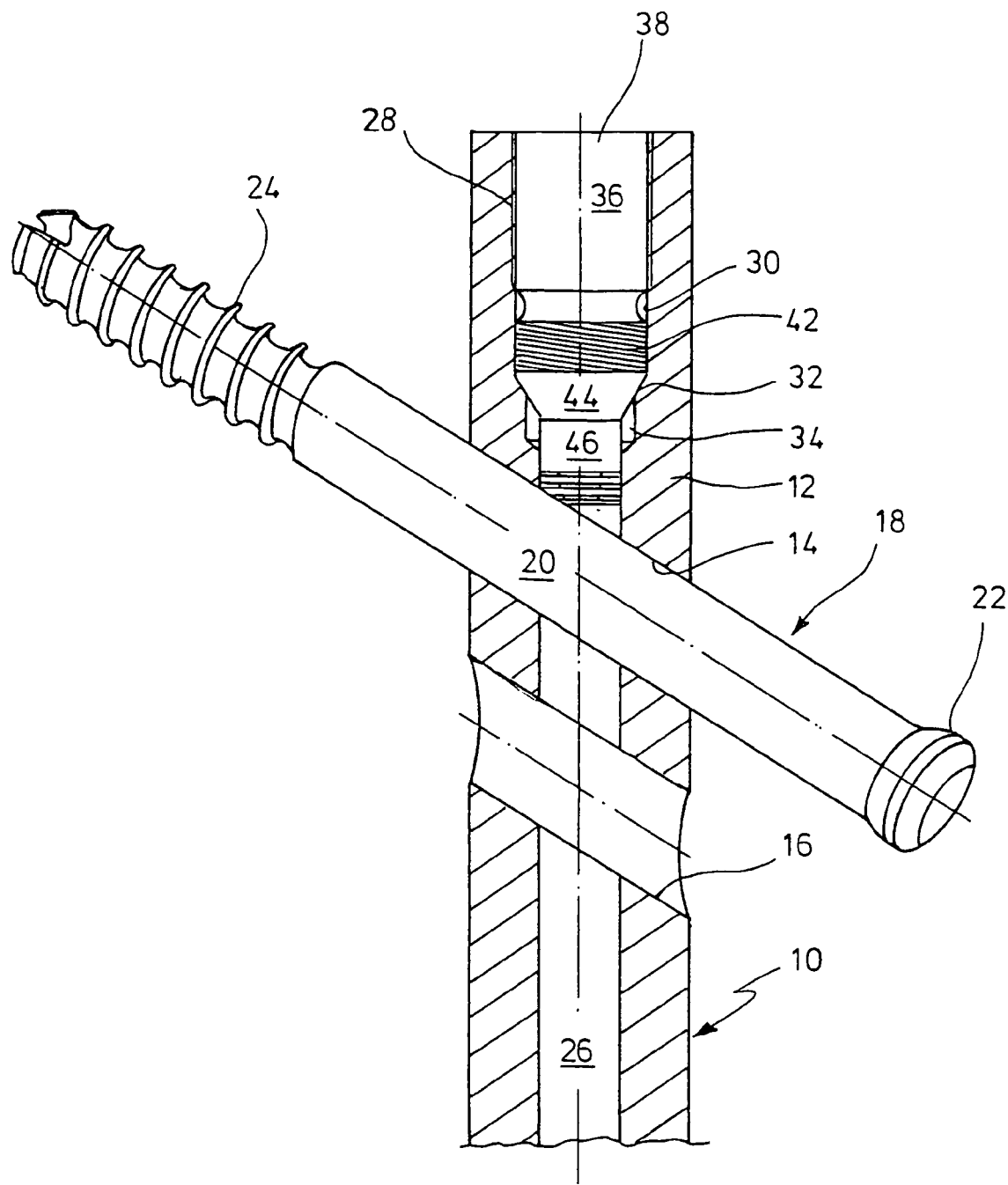
FIG. 1 is a cross-sectional view of the interlocking nail according to the invention.

Referring to FIG. 1, there is shown the proximal end of a femur interlocking nail 10 in a section with the preferred interlocking pin or screw of the present invention mounted therein. The distal portion of nail 10, which is not shown, preferably has at least one cross-bore to receive an interlocking screw as is well known. In the preferred embodiment, the proximal portion 12 of the nail shank has two parallel slanting bores 14, 16, each of which receive a femoral neck screw one of which is shown at 18. Of course, only a single cross-bore can be provided. In the preferred embodiment, the femoral neck screw 18 has a relatively long, smooth shank portion 20 one end of which has disposed thereon a head 22 and the other end of which has a threaded portion 24. Preferably, the thread 24 is self-cutting or self-tapping. The head 22 has provided thereon an appropriate receptacle for engagement by a rotating tool or driver (not shown).

Figure 2:
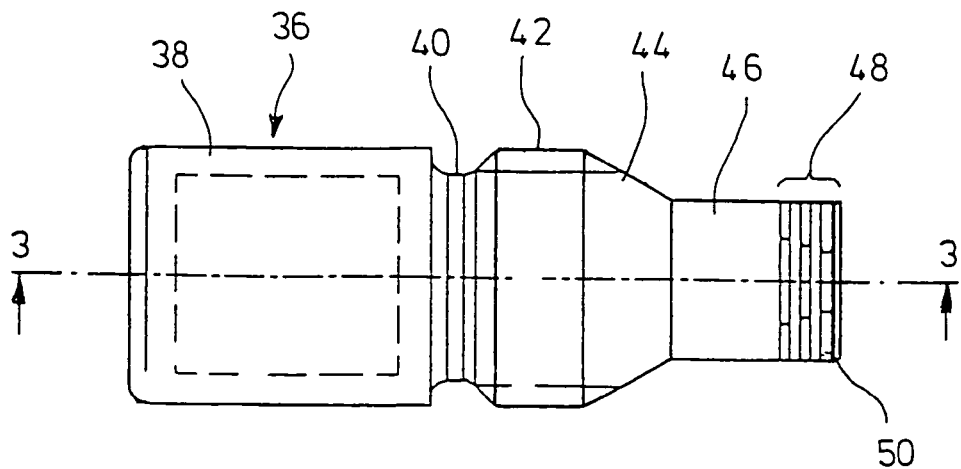
FIG. 2 is a side view of an interlocking pin for the interlocking nail of FIG. 1.
Figure 3:
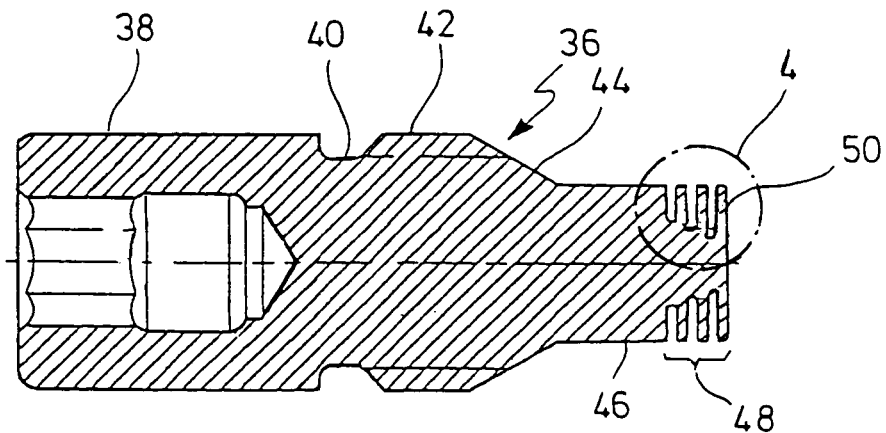
FIG. 3 is a cross-sectional view through the interlocking pin of FIG. 2 taken along line 3-3.
Figure 4:
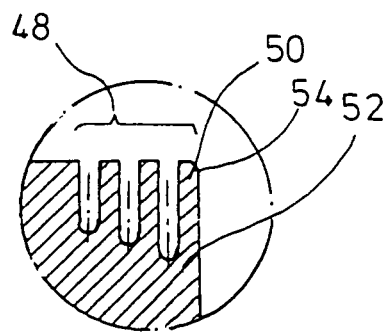
FIG. 4 shows the end part 4 of FIG. 3 in an enlarged scale.

Nail shank 10 has an axial bore 26 which is flared or enlarged towards the proximal end. In the preferred embodiment, bore 26 has a smooth bore portion 28, a threaded portion 30, a conical stop face 32, and a reduced diameter 34. The bore portions described above receive an interlocking pin or screw 36 which will be described in more detail below with reference to FIGS. 2 to 4.

The preferred locking pin or screw 36 has a first end with smooth cylindrical portion 38 which, towards a second pin end, is followed by an annular groove 40 which is then followed by a male threaded portion 42. The male threaded portion 42 is followed by a conical portion 44 which extends to end in a cylindrical portion 46. In the preferred embodiment, the cylindrical portion 46 has formed thereon three lamellar discs 48 as is more clearly shown in FIG. 4. Of course, more or fewer discs could be utilized.

In the preferred embodiment, the individual discs 50 of disc assembly 48 are circular and are spaced apart from each other at a predetermined uniform distance. They are connected to a central core portion 52 which increases in its diameter gradually moving from the pin second end towards the smooth portion 38. Thus, the free radial extent of each disc decreases on moving from the second pin end to the first pin end, although the outer diameter preferably remains constant. The disc portion 50 immediately adjacent the second pin end has a rounded or beveled end edge as can be recognized at 54.

While interlocking pin 36 is being inserted into nail shank portion 12, threaded portion 42 of interlocking pin 36 interengages with the female threaded portion 30 of nail shank 12. Screw or pin 36 is screwed in a distance until the stop face of conical portion 44 comes to bear against the stop face 32 of nail shank 12. Shortly before this, the front disc portions 50 come into engagement with smooth shank portion 20 of femoral neck screw 18 while being deformed as can be clearly seen in FIG. 1. Such deformation makes it possible to achieve an interlocking engagement when the stop face of interlocking pin 36 and proximal end 12 of nail 10 engage each other. The interlocking engagement is such as to cause a relatively large face area of the disc portions 50 to bear on the circumference of the shank portion 20 of the femoral neck screw 18, thus providing an efficient non-positive closure. The engagement is such as not to damage the neck screw shank portion 20.

In the preferred embodiment, the locking pin or screw 36 is made of a suitable material which is elastic, but is body-compatible.

It is plausible that the interlocking pin 36 can also be formed from two components, a metallic component being for the smooth portion 36 and threaded portion 42 and a plastic component being for the portion 46 and disc portions 50. If desired, the entire interlocking pin 36 can be formed from a plastic material such as, for example, polyethylene.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone nail comprising:
   a nail shank having at least one cross-bore adjacent a first end and an axial bore having a threaded portion, the cross-bore extending along an axis transverse to an axis of the axial bore;
   at least one screw having a threaded portion and a smooth shank portion between said threaded portion and a screw head, which can be introduced into the cross-bore; and
   an interlocking pin having a male threaded portion interacting with the threaded portion of the bore, and an end portion extending along an axis and having a plurality of lamellar discs extending generally perpendicular to the axis of the end portion wherein the end portion of the interlocking pin engages the smooth shank of the screw to locate it axially, and wherein at least said discs of said end portion of said pin are made of an elastically and/or plastically deformable material and deformable upon engaging the shank of the screw.

2. The bone nail as set forth in claim 1 wherein a plastic material is provided for the interlocking pin or end portion.

3. The bone nail as set forth in claim 1 wherein the interlocking pin or the end portion thereof is formed from an elastic material and the end portion has a compliant interlocking portion for engaging said screw in each rotational position of the interlocking pin.

4. The bone nail as set forth in claim 3 wherein the interlocking portion of the pin has a disc-shaped portion which is axially spaced from the adjacent part of the end portion and is joined to a central core portion.

5. The bone nail as set forth in claim 4 wherein the pin end portion includes a plurality of parallel axial disc-shaped portions which are joined to the core portion.

6. The bone nail as set forth in claim 5 wherein the plurality of disc-shaped portions have nearly the same outer diameter and the core portion gradually increases in diameter from the free end of the pin end portion.

7. The bone nail as set forth in claim 1 wherein the interlocking pin has a stop face which engages an abutment in the axial bore when the interlocking pin is in the interlocking position.

8. The bone nail as set forth in claim 7 wherein the interlocking pin has a smooth portion at an end opposite to the end portion and the male threaded portion is between the end portion and the smooth portion.

9. The bone nail as set forth in claim 1 wherein the screw is a femoral neck screw.

10. The bone nail as set forth in claim 9 wherein the nail shank has two axially spaced cross-bores for two parallel femoral neck screws.

11. A bone nail locking pin for a bone nail of the type having a shank with a threaded axial bore open to a first end of the nail and a cross-bore in communication with said axial bore for receiving a screw, the locking pin comprising:
   a first end for placement adjacent a proximal end of said nail;
   a second end for insertion into said cross-bore;
   a threaded portion extending between said first and second pin ends for engaging the threads of the axial bore in the nail shank; and
   a deformable portion at a free end of said second pin end for engaging a screw in said cross-bore wherein said deformable portion includes a plurality of discs surrounding a core wherein said core increases in diameter on moving from said second end to said first end and wherein the free radial extent of each disc increases on moving from said first to second end of said locking pin, the disc adjacent the free end deforming upon engaging the screw.

12. The locking pin as set forth in claim 11 wherein the interlocking pin has a stop face which engages an abutment in the nail axial bore when the locking pin is in engagement with the screw in the cross-bore.

13. The locking pin as set forth in claim 12 wherein the discs are made of a deformable plastic.

14. A bone nail locking system for locking a femoral neck screw in a femoral nail, comprising:
- a femoral nail having a longitudinal axis and having a cross-bore for receiving said femoral neck screw extending in a direction transverse to said axis at a proximal end of said nail and a threaded bore in the proximal nail end aligned with said longitudinal axis, said threaded bore and said cross-bore intersecting;
- a threaded locking pin having a first end for engaging a driver and a second end for contacting the femoral neck screw, said second end extending along an axis including at least one deformable radially extending lamellar disc extending generally perpendicular to the second end axis and adapted to contact the femoral neck screw, the disc deforming upon engaging the femoral neck screw.

15. The bone nail locking system as set forth in claim 14 wherein the second pin end includes a core portion including a plurality of discs, said core portion gradually increases in diameter on moving from said second pin end to said first pin end.

16. The bone nail locking system as set forth in claim 15 wherein the second pin end has a constant outer diameter and the free radial extent of the disc from the core increases on moving from said first to second pin end.

17. The bone nail locking system as set forth in claim 16 wherein said discs are made of a deformable polymeric material.

* * * * *

UNITED STATES PATENT AND TRADEMARK OFFICE
CERTIFICATE OF CORRECTION

PATENT NO. : 7,591,819 B2
APPLICATION NO. : 10/869190
DATED : September 22, 2009
INVENTOR(S) : Zander et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1332 days.

Signed and Sealed this

Twenty-first Day of September, 2010

David J. Kappos
*Director of the United States Patent and Trademark Office*